(12) United States Patent
Kim et al.

(10) Patent No.: US 10,767,174 B2
(45) Date of Patent: Sep. 8, 2020

(54) METHOD FOR RGEN RNP DELIVERY USING 5′-PHOSPHATE REMOVED RNA

(71) Applicant: INSTITUTE FOR BASIC SCIENCE, Daejeon (KR)

(72) Inventors: Jin-Soo Kim, Seoul (KR); So Jung Kim, Incheon (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 0 days.

(21) Appl. No.: 15/347,871

(22) Filed: Nov. 10, 2016

(65) Prior Publication Data

US 2017/0314016 A1  Nov. 2, 2017

(30) Foreign Application Priority Data

Nov. 13, 2015 (KR) .................. 10-2015-0159916
Mar. 25, 2016 (KR) .................. 10-2016-0036382

(51) Int. Cl.
| | |
|---|---|
| *C12N 15/63* | (2006.01) |
| *C12N 15/11* | (2006.01) |
| *C12N 15/113* | (2010.01) |
| *C12N 9/22* | (2006.01) |
| *A61K 48/00* | (2006.01) |
| *C12P 19/34* | (2006.01) |
| *C12N 15/10* | (2006.01) |

(52) U.S. Cl.
CPC ............ *C12N 15/11* (2013.01); *A61K 48/005* (2013.01); *C12N 9/22* (2013.01); *C12N 15/1024* (2013.01); *C12N 15/111* (2013.01); *C12N 15/63* (2013.01); *C12P 19/34* (2013.01); *C12N 2310/20* (2017.05); *C12N 2310/31* (2013.01); *C12N 2320/32* (2013.01); *C12N 2320/53* (2013.01); *C12N 2330/30* (2013.01)

(58) Field of Classification Search
None
See application file for complete search history.

(56) References Cited

U.S. PATENT DOCUMENTS

2015/0031132 A1    1/2015  Church et al.
2016/0355795 A1*  12/2016  Ran .......................... C12N 9/22

FOREIGN PATENT DOCUMENTS

| KR | 10-2015-0101476 | 9/2015 |
| WO | 2013-097965 | 7/2013 |

OTHER PUBLICATIONS

Prediger, E, Simplifying CRISPR, Tutorials, 2015, pp. 1-2.*
Prediger, E, 6 pieces of data that will change how you set up your CRISPR-Cas9 experiments, 2016, pp. 1-7.*
Zetsche et al, Cpf1 Is a Single RNA-Guided Endonuclease of a Class 2 CRISPR-Cas System, 2015, Cell 163, 1-13.*
Hendel et al, Chemically modified guide RNAs enhance CRISPR-Cas genome editing in human primary cells, Nat Biotechnol. Sep. 2015 ; 33(9): 985-989.*
Pichlmair, A., et al., "RIG-I-mediated antiviral responses to single-stranded RNA bearing 5′-phosphates", Science, vol. 314, p. 997-1001, Nov. 10, 2006.
Hornung, V., et al., "5′-Triphosphate RNA is the ligand for RIG-I", Science, vol. 314, p. 994-997 (2006), Nov. 10, 2006.
Kim, D.H., et al., "Interferon induction by siRNAs and ssRNAs synthesized by phage polymerase", Nature biotechnology vol. 22, No. 3, p. 321-325, Mar. 2004.

* cited by examiner

*Primary Examiner* — Maria Marvich
(74) *Attorney, Agent, or Firm* — Lex IP Meister, PLLC

(57) ABSTRACT

Provided are a composition for ribonucleoprotein delivery, comprising a guide RNA free of 5′-terminal phosphates, and a method for ribonucleoprotein delivery, using the same.

6 Claims, 10 Drawing Sheets
Specification includes a Sequence Listing.

METHOD FOR RGEN RNP DELIVERY USING 5'-PHOSPHATE REMOVED RNA

CROSS-REFERENCE TO RELATED APPLICATIONS

This application claims the benefits of Korean Patent Application No. 10-2015-0159916, filed on Nov. 13, 2015, and Korean Patent Application No. 10-2016-0036382, filed on Mar. 25, 2016, in the Korean Intellectual Property Office, the entire disclosures of which are hereby incorporated by reference.

BACKGROUND OF THE INVENTION

1. Field

The present disclosure relates to a composition for ribonucleoprotein delivery, comprising a guide RNA free of 5'-terminal phosphate, and a method for ribonucleoprotein using the same.

2. Description of the Related Art

The direct delivery of ribonucleoprotein (RNP), such as a complex of Cas9 protein and guide RNA or a complex of Cpf1 protein and crRNA, into cells (RNP delivery) is advantageous over general DNA delivery in many aspects. For example, RNP delivery can not only exclude the fragmentation of DNA upon genomic integration, but can also avoid cGAS activation attributed to the introduction of foreign DNA. In contrast to DNA delivery that requires time for the expression of proteins and RNAs, RNP readily acts as soon as it is introduced into cells, and degrades within 24 hrs after introduction, thus reducing off-target effects without sacrificing on-target activity.

There is a need for studies on side effects occurring upon RNP delivery into organisms and on solutions to avoid the side effects in order to effectively apply RNA to organisms.

BRIEF SUMMARY OF THE INVENTION

The present disclosure provides a technique of suppressing and/or mitigating the immune response induced by the delivery of a complex of RNA-guided endonuclease (RNA-guided endonuclease; RGEN), such as Cas9 protein or Cpf1 protein, and a guide RNA (ribonucleoprotein; RNP) into an organism, or a technique of reducing the consequent cytotoxicity, wherein the guide RNA is free of 5'-triphosphate.

An embodiment provides a composition for delivering an RNA-guided endonuclease (RGEN) ribonucleoprotein having decreased cytotoxicity into an organism, comprising a guide RNA free of a phosphate-phosphate bond at the 5' end thereof.

Another embodiment provides a method for delivering an RNA-guided endonuclease ribonucleoprotein into an organism, using a guide RNA free of a phosphate-phosphate bond at the 5' end thereof.

Another embodiment provides a method for reducing cytotoxicity upon the delivery of an RNA-guided endonuclease ribonucleoprotein into an organism, using a guide RNA free of a phosphate-phosphate bond at the 5' end thereof.

Another embodiment disclosure provides a method for preparing a guide RNA having reduced potential to induce an immune response and/or cytotoxicity, comprising removing 5'-terminal phosphate residues (e.g., di- and/or triphosphate) from the guide RNA, in detail, crRNA or sgRNA.

Another embodiment provides a method for preparing an RNA-guided endonuclease ribonucleoprotein having reduced potential to induce an immune response and/or cytotoxicity, comprising mixing a guide RNA (e.g., crRNA or sgRNA) free of a 5'-terminal phosphate-phosphate bond with an RNA-guided endonuclease (e.g., Cas protein or Cpf1 protein).

DETAILED DESCRIPTION OF THE INVENTION

Figure 1A:
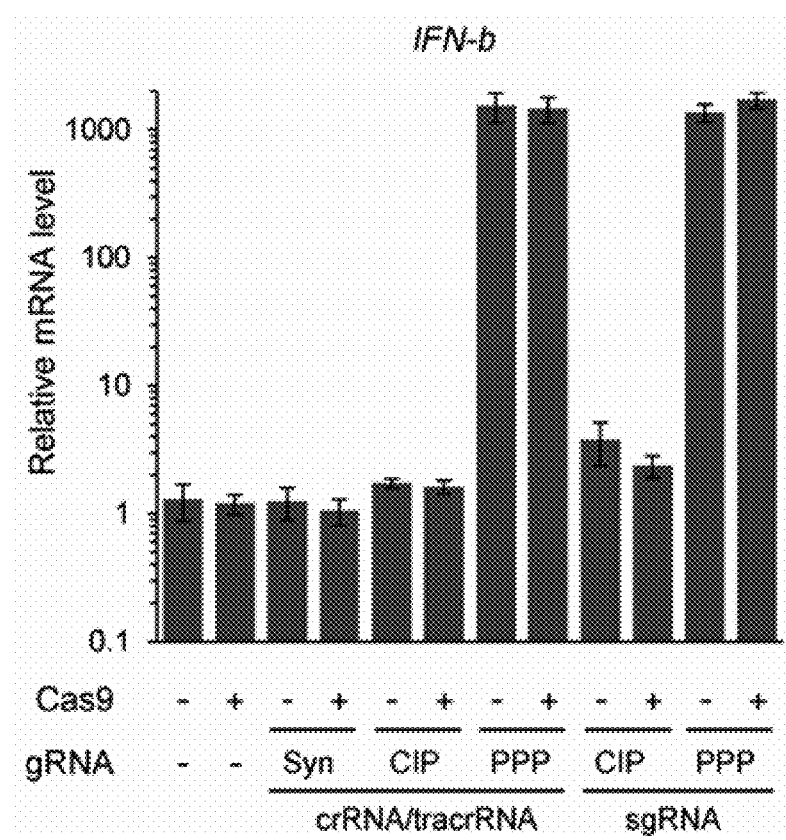
FIG. 1A is a graph showing IFN-β mRNA levels after the delivery of each of synthetic guide RNA, CIP-treated guide RNA, and in vitro transcribed guide RNA alone or in combination with Cas9 protein into the HeLa cell line, as measured by RT-qPCR.

Most of the guide RNAs involved in RNA-guided endonuclease ribonucleoproteins (RGEN RNPs) are synthesized by in-vitro transcription using bacteriophage-derived T7 RNA polymerase. In this regard, the T7 RNA polymerase leaves triphosphate at the 5' terminus of the generated guide RNA (5'-PPP). The 5'-triphosphate moiety of the guide RNA synthesized by in-vitro transcription is known to induce the expression of Type-1 interferons (IFN-α and IFN-β) in organisms, evoking immune responses and inducing the death of target cells. In addition, an immune response is evoked even when diphosphate is present at the 5-terminus of the guide RNA (5'-PP).

RNA-induced immune responses depend on various factors including the morphology of RNA, the kind, morphology and/or trait of a partner associated with RNA, and the external exposure (to intracellular environment), degree of exposure, and/or exposure site of RNA. The present disclosure first suggests that when an RGEN RNP, composed of a guide RNA having a specific morphology and an RGEN (e.g., Cas9, Cpf1, etc.) having a specific morphology and trait, exerts its function, the guide RNA can induce an immune response and show cytotoxicity (leading to the death of target cells) if it has a phosphate-phosphate bond at the 5' end (e.g. diphosphate and/or triphosphate).

It is also first provided in the present disclosure that a guide RNA free of (having no) phosphate-phosphate bonds (e.g. not having two or more phosphates) at the 5' end can be used in an RGEN RNP to suppress and/or mitigate the evocation of immune responses and to reduce cytotoxicity upon the delivery of the RGEN RNP into organisms.

As used herein, the term "cytotoxicity" is intended, unless otherwise stated, to mean the inhibition of cell survival and/or proliferation and/or the induction of cell damage, lysis and/or death by causing various phenomena harmful to cells, including immune response, metabolic inhibition, cellular component leakage, genetic modification, etc.

Unless otherwise state, the term "cytotoxicity reduction," as used herein, is intended to encompass phenomena not causing innate immunity, and/or mitigating (reducing) and/or removing (eliminating) the inhibition of cell survival and proliferation, and/or the induction of cell damage, lysis and/or death.

According to some embodiments thereof, the present disclosure provides a composition for RNA-guided endonuclease ribonucleoprotein delivery, comprising a guide RNA free of a phosphate-phosphate bond at the 5' end. The composition for RNA-guided endonuclease ribonucleoprotein delivery is significantly decreased in potential to induce immune responses and/or in cytotoxicity, compared to a composition comprising a guide RNA with a phosphate-phosphate bond (e.g. diphosphate or triphosphate) at the 5' end.

The composition for RNA-guided endonuclease ribonucleoprotein delivery may further comprise an RNA-guided endonuclease in addition to the guide RNA free of a 5'-terminal phosphate-phosphate bond. The RNA-guided endonuclease may be at least one selected from the group consisting of a Cas9 protein and a Cpf1 protein.

Another embodiment of the present disclosure addresses a method for delivering RNA-guided endonuclease ribonucleoprotein into an organism using a guide RNA free of a 5'-terminal phosphate-phosphate bond.

This method is significantly decreased in potential to induce immune responses and/or in cytotoxicity, compared to a method using a guide RNA with a phosphate-phosphate bond (e.g., diphosphate or triphosphate) at the 5' end.

Accordingly, contemplated in accordance with another embodiment of the present disclosure is a method for reducing cytotoxicity upon the delivery of an RNA-guided endonuclease ribonucleoprotein into an organism, using a guide RNA free of a 5'-terminal phosphate-phosphate bond.

The delivery method and/or the cytotoxicity-reducing method may comprise administering a mixture of a guide RNA, free of a 5'-terminal phosphate-phosphate bond, and an RNA-guided endonuclease into an organism. The RNA-guided endonuclease may be at least one selected from the group consisting of a Cas9 protein and a Cpf1 protein.

As used herein, the term "RNA-guided endonuclease ribonucleoprotein" refers to a protein-ribonucleic acid complex containing an RNA-guided endonuclease and a guide RNA, and the term "ribonucleoprotein", unless otherwise specified, is interchangeably used with "RNA-guided endonuclease ribonucleoprotein".

As used herein, the term "endonuclease" refers to an enzyme that complexes with a single- or double-stranded RNA and creates a site-specific cleavage in a target DNA sequence complementary to the RNA, thus performing genome-editing. Representative among such endonucleases are Cas9 (CRISPR-associated protein 9) and Cpf1 (CRISPR from *Prevotella* and *Francisella* 1), which are used in Type II and Type V CRISPR/Cas systems, respectively.

The Cas9 protein may be an endonuclease derived from *Streptococcus* sp.), for example, *Streptococcus pyogenes*) (Swiss rot Accession number Q99ZW2), but is not limited thereto.

Examples of the Cpf1 protein include those derived from Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), *Candidatus methanoplasma termitum*, and *Eubacterium eligens*, but are not limited thereto. Particularly, the Cpf1 protein may be an endonuclease derived from Parcubacteria bacterium (GWC2011_GWC2_44_17), Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Leptospira inadai*, Lachnospiraceae bacterium (MA2020), *Francisella novicida* (U112), *Candidatus methanoplasma termitum*, or *Eubacterium eligens*.

The endonuclease such as Cas9 or Cpf1 may be an enzyme isolated from microorganisms, or a non-naturally occurring enzyme produced through a recombination or synthesis method. Optionally, the endonuclease may further comprise an element typically used for import into cell nuclei by nuclear transport in eukaryotes (e.g., nuclear localization signal: NLS).

As described above, the guide RNA used in the composition or method for RNA-guided endonuclease ribonucleoprotein delivery according to the present disclosure does not contain a phosphate-phosphate bond at the 5' end. The term "phosphate-phosphate bond," as used herein, refers to an ester bond formed between two phosphate molecules. Therefore, the guide RNA free of a 5'-terminal phosphate-phosphate bond means a guide RNA that does not have a phosphate-phosphate bond at the 5' end, that is, neither 5'-terminal diphosphate nor 5'-terminal triphosphate. Thus, the expression "the guide free of 5'-terminal phosphate-phosphate bonds" is intended to encompass a guide RNA with a monophosphate or OH group at the 5' end, and a guide RNA having any possible modified 5' end without causing cytotoxicity in eukaryotic cells or organisms other than pathogens such as viruses or bacteria (for example, a 5' end naturally or artificially modified for immunosuppression, safety, labeling, etc.).

When used to synthesize a guide RNA for the RNA-guided endonuclease ribonucleoprotein through in-vitro transcription with nucleoside triphosphates (NTPs) serving as a substrate, a prokaryotic RNA polymerase, such as T7 RNA polymerase (polymerase from T7 bacteriophage), exhibits an advantage over a eukaryotic RNA polymerase in terms of productivity. The nascent guide RNA synthesized through in-vitro transcription by a prokaryotic RNA polymerase such as T7 RNA polymerase has an intact 5' end. That is, because the nascent guide RNA does not undergo modification, it has triphosphate at the 5' end (PPP-5'). The prokaryotic RNA polymerase may be an RNA polymerase from a bacteriophage, for example, at least one selected from the group consisting of T7 RNA polymerase, T3 RNA polymerase, and SP6 RNA polymerase, but is not limited thereto. So long as it synthesizes RNA with triphosphate left at the 5' end, any prokaryotic (e.g., bacteriophage) RNA polymerase may be employed.

As such, a guide RNA with a 5'-terminal triphosphate, when delivered (introduced) into an organism, activates interferon activity or stimulates the expression of interferon response genes to induce an immune response. Compared to a guide RNA with an intact 5' end (with a 5'-terminal triphosphate), a guide RNA (e.g., crRNA or sgRNA) from which the 5'-terminal triphosphate (e.g., two or more 5'-terminal triphosphates) is removed or which is synthesized with no triphosphate residues present at the 5' end thereof was found to induce a significantly decreased level of interferon and/or genes involved in interferon responses, suppressing the evocation of immune responses (Examples 1.2, 1.3, and 2.2) and decreasing cytotoxicity (that is, remarkably increasing cell viability; Example 1.4). In addition, the guide RNA (i.e. crRNA or sgRNA) from which the 5'-terminal triphosphate is removed or which is synthesized with no triphosphate residue present at the 5' end thereof was observed to have no influence on genome editing/proofreading at a target site (Examples 1.5 and 2.3).

For use in the present disclosure, therefore, a guide RNA may be synthesized through in-vitro transcription using a prokaryotic RNA polymerase such as T7 RNA polymerase and then through chemical or enzymatic modification to remove two or more phosphate residues (e.g., di- or triphosphate) from the three phosphate residues at the 5' end.

As used herein, the expression "removal of the 5'-terminal phosphate" means the removal of two or three phosphate residues (e.g., di- or triphosphate) from the tree phosphate residues at the 5' end.

The removal of the 5'-terminal phosphate, for example, the removal of two or more phosphate residues (e.g., di- or triphosphate) at the 5' end, may be achieved using any method that breaks the ester bond between phosphate residues to isolate two or more phosphate residues from RNA. For example, a phosphatase may be used to perform the removal. The phosphatase may be at least one selected from the group consisting of calf intestinal alkaline phosphatase (CIP), shrimp alkaline phosphatase (SAP), and Antarctic phosphatase, but is not limited thereto. So long as it functions to isolate a phosphate residue from RNA, any enzyme may be used.

The guide RNA may be selected depending on the kind and/or source microorganism of an endonuclease to be associated therewith. For instance, the guide RNA may be at least one selected from the group consisting of CRISPR RNA (crRNA), trans-activating crRNA (tracrRNA), and single guide RNA (sgRNA). Depending on the kind of endonuclease, CRISPR RNA (crRNA) alone, a complex of CRISPR RNA (crRNA) and trans-activating crRNA (tracrRNA), or single guide RNA (sgRNA) may be used as the guide RNA.

By way of example, a Cas9 protein-containing complex (Cas9 system) needs two guide RNAs, that is, CRISPR RNA (crRNA), having a nucleotide sequence hybridizable with a target region of DNA, and an additional trans-activating crRNA (tracrRNA), wherein the crRNA and the tracrRNA are combined to each other to form a duplex or are connected to each other through a linker to form a single guide RNA (sgRNA). For use in editing/proofreading a target gene, a Cpf1 protein-containing complex (Cpf1 system) needs one guide RNA, that is, crRNA having a nucleotide sequence hybridizable with a target region of DNA.

The sequence of the guide RNA may be selected depending on the kind of Cas9 or Cpf1 (source microorganisms), and is readily determined by a person of ordinary skill in the art.

In one particular embodiment of the present disclosure, crRNA useful in the Cas9 system containing a Cas9 protein derived from *Streptococcus pyogenes* may be represented by the following Formula 1:

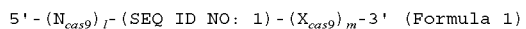

wherein, $N_{cas9}$ is a targeting sequence region hybridizable with a target region of DNA and is determined depending on the target region of DNA, and l represents an integer number of nucleotides present in the targeting sequence region, ranging from 18 to 22, for example, being 20;

the 12 consecutive nucleotides (GUUUUAGAGCUA; SEQ ID NO: 1), located adjacent to the 3' end of the targeting sequence region, are an essential region of crRNA; and $X_{cas9}$ represents a group of nucleotides located adjacent to the 3' end of crRNA (that is, the essential region of crRNA), and m is an integer of 8 to 12, for example, 10, wherein the nucleotides may be the same or different and are each independently selected from the group consisting of A, U, C, and G.

As used in the context of the present disclosure, a nucleotide sequence hybridizable with a target region of DNA means having a sequence identity at least 50%, at least 60%, at least 70%, at least 80%, at least 90%, at least 95% or at least 99%, or 100% homologous to the nucleotide sequence of the target region (hereinafter, used as the same meaning unless otherwise stated).

For example, $X_{cas9}$ may contain UGCUGUUUUG (SEQ ID NO: 2), but is not limited thereto.

In another particular embodiment of the present disclosure, tracrRNA useful in the Cas9 system containing a Cas9 protein derived from *Streptococcus pyogenes* may be represented by the following Formula 2:

5'-(Y$_{cas9}$)$_p$-(SEQ ID NO: 3)-3'    (Formula 2)

wherein,
the 60 nucleotide residues (UAG-CAAGUUAAAAUAAGGCUAGUCCGUUAUCAAC-UUGAAAAAGUGGCACCG AGUCGGUGC; SEQ ID NO: 3) are an essential region of tracrRNA; and Y$_{cas9}$ represents a group of nucleotides located adjacent to 5' end of the essential region of tracrRNA, and p is an integer of 6 to 20, and particularly 8 to 19, wherein the nucleotides may be the same or different and are each independently selected from the group consisting of A, U, C, and G.

In addition, sgRNA useful in the Cas9 system containing a Cas9 protein derived from *Streptococcus pyogenes* has a hairpin structure in which a crRNA region, comprising the targeting sequence region and the essential region of the crRNA, and a tracrRNA region, comprising the essential region of the tracrRNA, are linked to each other via a nucleotide linker. In greater detail, the sgRNA has a hairpin structure in which a crRNA region comprising the targeting sequence region and the essential region of the crRNA is partially hybridized with a tracrRNA region comprising the essential region of the tracrRNA to form a duplex RNA, with a linkage between the 3' end of the crRNA region and the 5' end of the tracrRNA region via a nucleotide linker.

The targeting sequence region, the essential region of the crRNA, and the essential region of the tracrRNA are respectively as described above. The nucleotide linker contained in the sgRNA is 3 to 5 nucleotides long, for example, 4 nucleotides long, wherein the nucleotides may be the same or different and are each independently selected from the group consisting of A, U, C, and G.

The crRNA (represented by Formula 1) or sgRNA of the Cas9 protein may further comprise 1 to 3 guanine (G) residues at the 5' end (that is, the 5' end of crRNA).

The tracrRNA or sgRNA of the Cas9 protein may further comprise a terminal region consisting of 5 to 7 uracil (U) residues at the 3' end of the essential region (60 nt) of tracrRNA.

In another embodiment of the present disclosure, the crRNA useful in the Cpf1 system containing a Cpf1 protein is represented by the following Formula 3:

5'-(SEQ ID NO: 4)-(N$_{cpf1}$)$_q$-3'    (Formula 3)

wherein,
n1 is U, A, or G, n2 is A or G, n3 is U, A, or C, n4 is G, C, or A or represents the absence of nucleotide residues, and n5 is A, U, C, or G, N$_{cpf1}$ is a targeting sequence region hybridizable with a target region of DNA and is determined depending on the target region of DNA, and q represents an integer number of nucleotides present in the targeting sequence region, ranging from 17 to 24, for example, from 18 to 23.

In Formula 3, the five nucleotide residues at positions 6 to 10 from the 5' end (5'-terminal stem region) and the five nucleotide residues at positions 15 to 19 (16 to 20 if n4 is present) (3'-terminal stem region) are complementary to each other in an anti-parallel direction to form a duplex (a stem structure), while the three to five nucleotide residues between the 5'-terminal region and the 3'-terminal region are responsible for a loop structure.

According to an embodiment, the crRNA of the Cpf1 protein may not contain the first nucleotide (n1) of Formula 3.

The crRNA of the Cpf1 protein (e.g., represented by Formula 3) may further contain one to three guanine (G) residues at the 5' end.

Available 5'-terminal sequences of the crRNA of Cpf1 protein depending on the microorganism from which Cpf1 was derived are given as shown in Table 1 (exclusive of the targeting sequence region):

TABLE 1

| Cpf1-derived Microorganism | 5'-Terminal Sequence of Guide RNA (crRNA)(5'-3') | SEQ ID NO: |
|---|---|---|
| *Parcubacteria bacterium* GWC2011_GWC2_44_17 (PbCpf1) | AAAUUUCUACU-UUUGUAGAU | 5 |
| *Peregrinibacteria bacterium* GW2011_GWA_33_10 (PeCpf1) | GGAUUUCUACU-UUUGUAGAU | 6 |
| *Acidaminococcus sp.* BVBLG (AsCpf1) | UAAUUUCUACU-CUUGUAGAU | 7 |
| *Porphyromonas macacae* (PmCpf1) | UAAUUUCUACU-AUUGUAGAU | 8 |
| *Lachnospiraceae bacterium* ND2006 (LbCpi1) | GAAUUUCUACU-AUUGUAGAU | 9 |
| *Porphyromonas crevioricanis* (PcCpf1) | UAAUUUCUACU-AUUGUAGAU | 10 |
| *Prevotella disiens* (PdCpf1) | UAAUUUCUACU-UCGGUAGAU | 11 |
| *Moraxella bovoculi* 237 (MbCpf1) | AAAUUUCUACUGUUUGUAGAU | 12 |
| *Leptospira inadai* (LiCpf1) | GAAUUUCUACU-UUUGUAGAU | 13 |
| *Lachnospiraceae bacterium* MA2020 (Lb2Cpf1) | GAAUUUCUACU-AUUGUAGAU | 14 |
| *Francisella novicida* U112 (FnCpf1) | UAAUUUCUACU-GUUGUAGAU | 15 |
| *Candidatus Methanoplasma termitum* (CMtCpf1) | GAAUCUCUACUCUUUGUAGAU | 16 |
| *Eubacterium eligens* (EeCpf1) | UAAUUUCUACU--UUGUAGAU | 17 |

("-" denotes omitted nucleotides)

Here, the guide RNA is as described above and is at least one selected from the group consisting of crRNA, tracrRNA, and sgRNA.

The composition or the method for RNA-guided endonuclease ribonucleoprotein delivery (or the method for reducing cytotoxicity), proposed in the present disclosure, is characterized by lacking the ability to induce the expression of interferon and/or genes involved in interferon responses during ribonucleoprotein delivery into an organism, with the consequent suppression, mitigation, or reduction of immune responses and cytotoxicity.

In the composition for RNA-guided endonuclease ribonucleoprotein delivery according to the present disclosure, the organism to which the RNA-guided endonuclease ribonucleoprotein is delivered may be selected from the group consisting of all eukaryotic cells (e.g. fungi such as yeast, cells derived from eukaryotic animals and/or eukaryotic organisms (embryos, stem cells, somatic cells, gametes, etc.) and the like), eukaryotic animals (e.g. primates such as humans, apes, etc., dogs, pigs, cow, sheep, goats, mice, rats, etc.), and eukaryotic plants (e.g. algae such as green algae, maize, wheat, rice, etc.).

In the method for RNA-guided endonuclease ribonucleoprotein delivery or the method for reducing cytotoxicity according to the present disclosure, the organism to which the RNA-guided endonuclease ribonucleoprotein is delivered may be selected from the group consisting of all eukaryotic cells (e.g. fungi such as yeast, cells derived from eukaryotic animals and/or eukaryotic organisms (embryos, stem cells, somatic cells, gametes, etc.) and the like), eukaryotic animals (e.g. primates such as humans, apes, etc., dogs, pigs, cow, sheep, goats, mice, rats, etc.), and eukaryotic plants (e.g. algae such as green algae, maize, wheat, rice, etc.). In an embodiment of the method for RNA-guided endonuclease ribonucleoprotein delivery, the eukaryotic animals may be animals other than humans, and the eukaryotic cells may be those isolated from eukaryotic animals including humans.

The RNA-guided endonuclease ribonucleoprotein delivery may be achieved either through an appropriate vector or by direct intracellular introduction (in a non-vector manner), e.g., electroporation, or with the aid of a typical transfection reagent (e.g., Lipofectamine).

Contemplated in accordance with another embodiment of the present disclosure is a method for preparing a guide RNA having reduced potential to induce an immune response and cytotoxicity, or a method for reducing the potential of guide RNA to induce an immune response and cytotoxicity, comprising removing two or more phosphate residues (e.g., di- and/or triphosphate) from a guide RNA after the guide RNA is synthesized through in-vitro transcription using a prokaryotic RNA polymerase.

The preparing or reducing method may comprise:
(1) providing a guide RNA that is prepared through in-vitro transcription in the presence of a prokaryotic RNA polymerase; and
(2) removing two or more phosphate residues (e.g., di- and/or triphosphate) from the 5'-terminal phosphate of the guide RNA.

When synthesized through in-vitro transcription using a prokaryotic RNA polymerase, the guide RNA retains, as described above, a triphosphate residue at the 5' end thereof.

The eukaryotic RNA polymerase may be a bacteriophage RNA polymerase, for example, at least one selected from the group consisting of T7 RNA polymerase, T3 RNA polymerase, and SP6 RNA polymerase, but is not limited thereto. So long as it leaves a triphosphate residue at the 5' end of a nascent RNA molecule, an RNA polymerase from any prokaryotic cell (e.g. bacteriophage) may be employed.

The removal of two or more phosphate residues from the 5' end of the guide RNA may be achieved using any method that breaks the ester bond between phosphate residues to isolate two or more phosphate residues from RNA. For example, a phosphatase may be used to perform the removal. The phosphatase may be at least one selected from the group consisting of calf intestinal alkaline phosphatase (CIP), shrimp alkaline phosphatase (SAP), and Antarctic phosphatase, but is not limited thereto. So long as it functions to isolate a phosphate residue from RNA, any enzyme may be used.

According to another embodiment thereof, the present disclosure addresses a method for preparing an RNA-guided endonuclease ribonucleoprotein having reduced potential to induce an immune response and cytotoxicity, or a method for reducing the potential of a RNA-guided endonuclease ribonucleoprotein to induce an immune response and cytotoxicity, comprising mixing a guide RNA free of a 5'-terminal phosphate-phosphate bond (e.g. di- and/or triphosphate) with a Cas9 protein or a Cpf1 protein. The guide RNA free of a 5'-terminal phosphate-phosphate bond may be prepared using the above-stated preparation method (comprising steps (1) and (2)), or may be chemically synthesized to have a monophosphate residue or an OH group at the 5' end or to have any possible modified 5' end without causing cytotoxicity in eukaryotic cells or organisms other than pathogens such as viruses or bacteria (for example, a 5' end naturally or artificially modified for immunosuppression, safety, labeling, etc.).

All of the steps in the method for preparing a guide RNA or an RNA-guided endonuclease ribonucleoprotein may be performed in vivo or in vitro.

Designed to prevent and/or mitigate the induction of immune responses during RGEN RNP by employing a guide RNA free of di- or triphosphate at the 5' end, the present disclosure is applicable for the development of an effective RGEN-based therapeutic agent having reduced side effects.

EXAMPLES

A better understanding of the present disclosure may be obtained through the following examples which are set forth to illustrate, but are not to be construed to limit the present disclosure.

Example 1: CAs9 RNP Delivery 1.1: Preparation of Guide RNA crRNA and tracrRNA, each of which was prepared through in-vitro transcription (PPP-crRNA/PPP-tracrRNA) or through a chemical synthesis method (Syn-crRNA/Syn-tracrRNA), were used as guide RNAs for targeting an HBB (human beta-globin) gene. A single-chain guide RNA (sgRNA) targeting an HBB gene was prepared through in-vitro transcription (T7 promoter) (PPP-sgRNA).

For the in-vitro transcription, respective oligomers (Table 2) were annealed with corresponding RNAs and then extended using Phusion polymerase (NEB) to give templates, followed by a T7 RNA polymerase (NEB) reaction on the templates.

TABLE 2

Oligomer Sequences as in vitro Transcription Templates

5'→3'

| | | | |
|---|---|---|---|
| sgRNA_F | GAAATTAATACGACTCACTATAgTTGCCCCACAGGGCAGTAAGT TTTAGAGCTAGAAATAGCAAG | 65 mer | SEQ ID NO: 18 |

TABLE 2-continued

Oligomer Sequences as in vitro Transcription Templates

5'→3'

| | | | |
|---|---|---|---|
| sgRNA_R | AAAAAAGCACCGACTCGGTGCCACTTTTTCAAGTTGATAACGGA CTAGCCTTATTTTAACTTGCTATTTCTAGCTCTAAAAC | 80 mer | SEQ ID NO: 19 |
| crRNA_F | GAAATTAATACGACTCACTATAgTTGCCCCACAGGGCAGTAAGT TTTAGAGCTATGCTGTTTTG | 64 mer | SEQ ID NO: 20 |
| crRNA_R | CAAAACAGCATAGCTCTAAAACTTACTGCCCTGTGGGGCAAcTA TAGTGAGTCGTATTAATTTC | 64 mer | SEQ ID NO: 21 |
| tracRNA_F | GAAATTAATACGACTCACTATAGGAACCATTCAAAACAGCATAGC AAGTTAAAATAAGGCTAGTCCG | 67 mer | SEQ ID NO: 22 |
| tracRNA_R | AAAAAAAGCACCGACTCGGTGCCACTTTTTCAAGTTGATAACGG ACTAGCCTTATTTTAACTTGCTATG | 69 mer | SEQ ID NO: 23 |

(underlined (20 nt): X20 sequence (HBB-targeting sequence; suitably designed to be hybridizable with a target gene))

Each of the RNAs prepared through in-vitro transcription was treated with calf intestinal alkaline phosphatase (CIP; NEB) in an amount of 250 U per 200 µl reaction, and subjected to phenol/chloroform extraction. Subsequently, column purification afforded 5'-triphosphate-free RNAs (CIP-crRNA/CIP-tracrRNA/CIP-sgRNA) (Table 3).

TABLE 3

Guide RNA Sequence of RGEN (Cas9)

| | Sequence (5' - 3') | length | SEQ ID NO: |
|---|---|---|---|
| PPP-sgRNA/ CIP-sgRNA | GUUGCCCCACAGGGCAGUAA*GUUUUAGAGCUA*GA AAUAGCAAGUUAAAAUAAGGCUAGUCCGUUAUCA ACUUGAAAAAGUGGCACCGAGUCGGUGCUUUUUU U | 102 nt | 24 |
| PPP-crRNA/ CIP-crRNA/ Syn-crRNA | GUUGCCCCACAGGGCAGUAA*GUUUUAGAGCUA*UG CUGUUUUG | 42 nt | 25 |
| PPP-tracrRNA/ CIP-tracrRNA | GGAACCAUUCAAAACAGCAUAGCAAGUUAAAAUA AGGCUAGUCCGUUAUCAACUUGAAAAAGUGGCA CCGAGUCGGUGCUUUUUUU | 86 nt | 26 |
| Syn_tracrRNA | AAACAGCAUAGCAAGUUAAAAUAAGGCUAGUCCG UUAUCAACUUGAAAAAGUGGCACCGAGUCGGUG CU | 69 nt | 27 |

(underlined: HBB-targeting sequence; italics: crRNA-derived sequence; bold: tracr-RNA-derived sequence; underlined + bold: linker)

1.2: mRNA Level of Genes Involved in Type I Interferon Response

For Cas9 RNP delivery, a *Streptococcus pyogenes*-derived Cas9 protein (4.4 µg, 25 pmol) was mixed with the HBB gene-targeting guide RNA prepared in Example 1.1, that is, crRNA/tracrRNA or sgRNA (25 pmol). Using a Lipofectamine 2000 (Invitrogen) reagent, transfection (Cas9 alone or in combination with the guide RNA mixture) into a human HeLa cell line (ATCC) was performed. After 24 hrs of incubation, the media were taken and used in IFN-beta ELISA. The cells were lysed to obtain total RNA. After 48 hrs of incubation, genomic DNA was isolated and measured for the efficiency of RGEN RNP-derived mutation.

Using the total RNA, RT-qPCR was conducted to measure mRNA levels of IFN-β (Interferon-beta), RIG-I (retinoic acid-inducible gene 1), and OAS2 (2'-5'-oligoadenylate synthetase 2) genes known to be up-regulated by Type I interferon response. The primers used in the RT-qPCR are summarized in Table 4, below.

TABLE 4

| Beta-actin-F | CCCAGCCATGTACGTTGCTA (SEQ ID NO: 28) | Beta-actin-R | TCACCGGAGTCCATCACGAT (SEQ ID NO: 29) |
|---|---|---|---|
| IFN-b-F | TGCTTCTCCACTACAGCTCTT (SEQ ID NO: 30) | IFN-b-R | GCAGTATTCAAGCCTCCCAT (SEQ ID NO: 31) |
| OAS2-F | TCAGAAGAGAAGCCAACGTGA (SEQ ID NO: 32) | OAS2-R | CGGAGACAGCGAGGGTAAAT (SEQ ID NO: 33) |
| RIG-1-F | GGACGTGGCAAAACAAATCAG (SEQ ID NO: 34) | RIG-1-R | GCAATGTCAATGCCTTCATCA (SEQ ID NO: 35) |

Expression levels of the genes (mRNA levels) are depicted in FIGS. 1A (IFN-β), 1B (RIG-I), and 10 (OAS2) (Syn: synthetic crRNA & tracrRNA (free of 5'-triphospate); CIP: CIP-treated in vitro transcript (free of 5'-triphospate); PPP: in vitro transcript (having 5'-triphospate)).

Figure 1B:
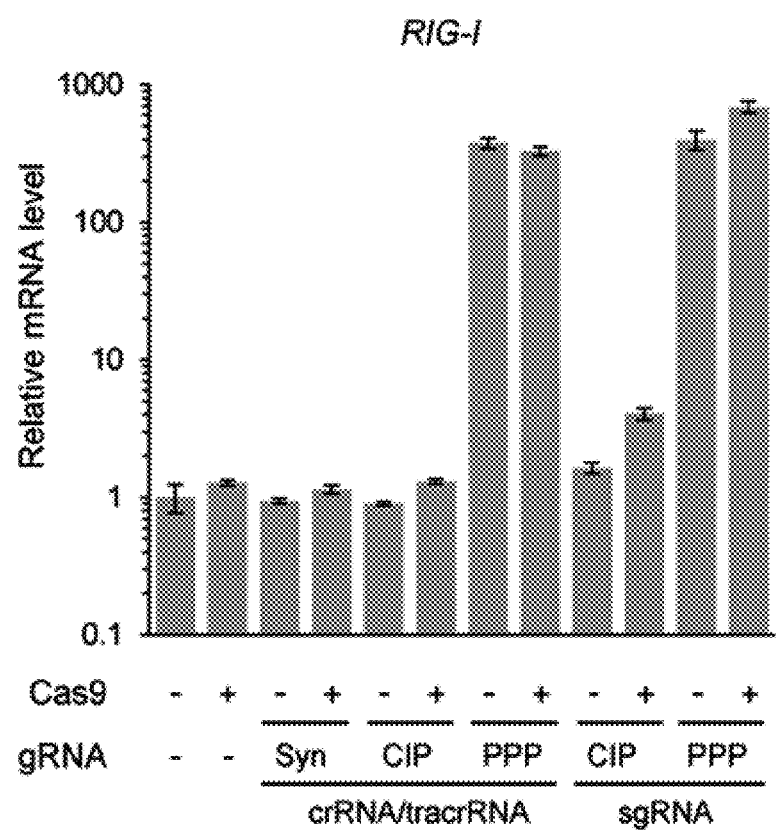
FIG. 1B is a graph showing RIG-I mRNA levels after the delivery of each of synthetic guide RNA, CIP-treated guide RNA, and in vitro transcribed guide RNA alone or in combination with Cas9 protein into the HeLa cell line, as measured by RT-qPCR.
Figure 1C:
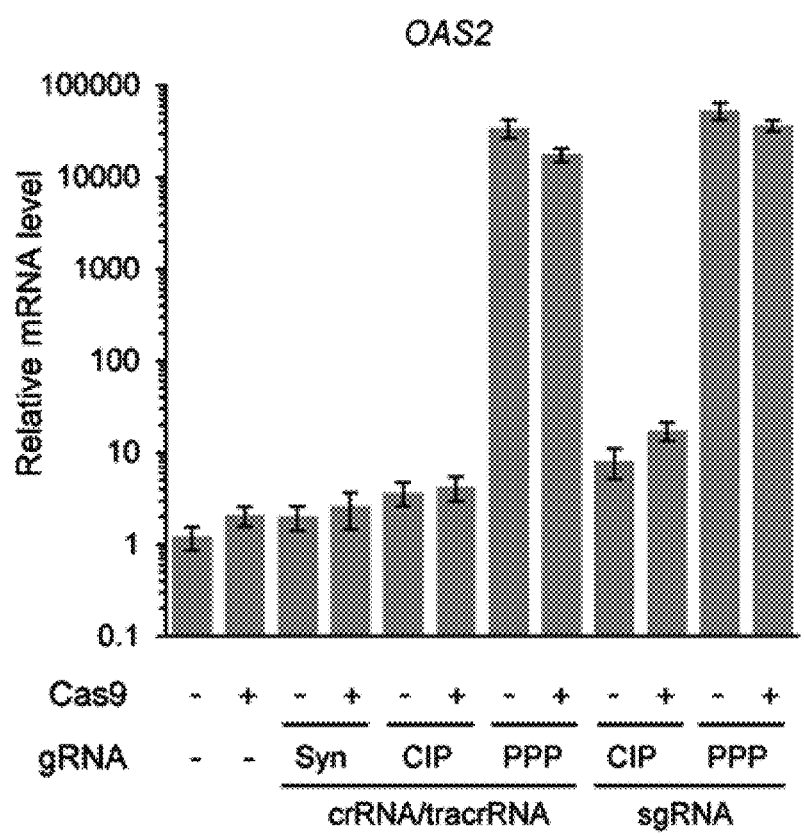
FIG. 1C is a graph showing OAS2 mRNA levels after the delivery of each of synthetic guide RNA, CIP-treated guide RNA, and in vitro transcribed guide RNA alone or in combination with Cas9 protein into the HeLa cell line, as measured by RT-qPCR.

As shown in FIGS. 1A-1C, the synthetic guide RNA or the CIP-treated guide RNA both having 5'-OH (that is, free of 5'-triphosphate), allowed IFN-β, RIG-I, and OAS2 genes to be expressed in levels similar to the background level detected in the sample of mock transfection, regardless of whether the Cas9 protein was used. In contrast, treatment with the in-vitro-transcribed PPP-crRNA/PPP-tracrRNA or PPP-sgRNA increased each of IFN-β and RIG-I genes by about 100 times and the OAS2 gene by about 10,000 times. These results indicate the 5'-triphosphate present in the guide RNA of Cas9 RNP induces Type I interferon response. It was also observed that the synthetic RNA or the CIP-treated guide RNA can be used to avoid the immune response.

1.3: IFN-β Protein Level

To examine the change in IFN-β protein level, a Cas9 protein was delivered (transfected), alone or in combination with each of the guide RNAs prepared in Example 1.1, into the HeLa cell line (ATCC). Twenty four hours after transfection, IFN-β ELISA was performed using a VeriKine™ Human IFN Beta ELISA Kit to quantitatively analyze IFN-β protein levels.

Figure 2:
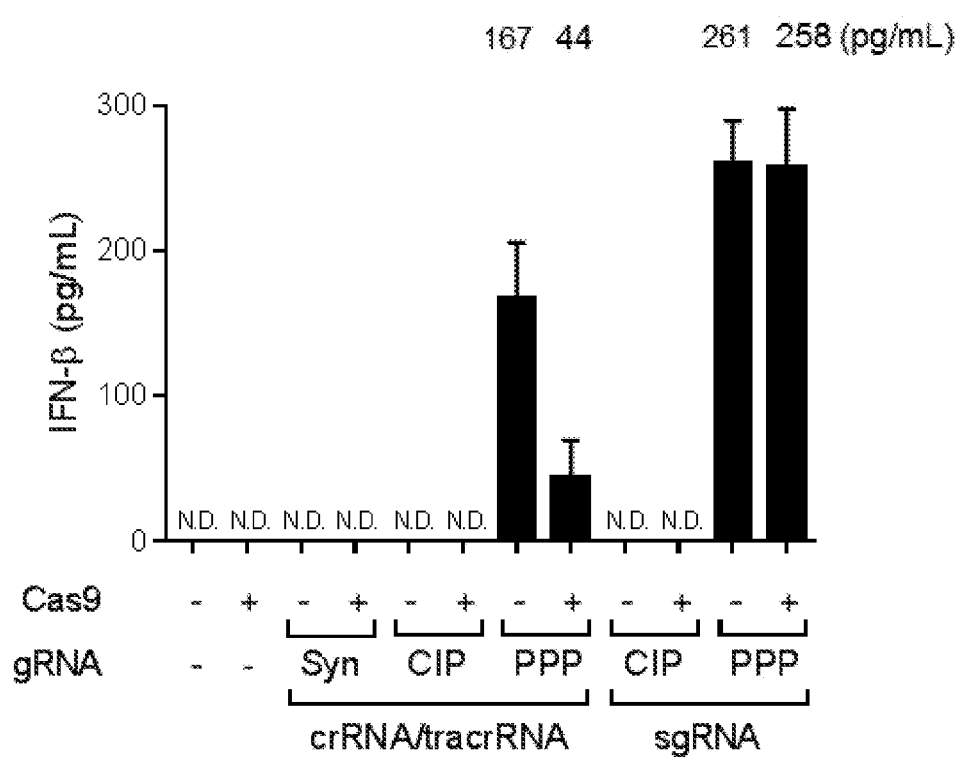
FIG. 2 is a graph showing secreted IFN-6 protein levels after the delivery of each of the synthetic guide RNA, CIP-treated guide RNA, and in-vitro transcribed guide RNA alone or in combination with Cas9 protein into the HeLa cell line, as measured by ELISA (N.D.: None detected)

The results are shown in FIG. 2 (mean of triplicate measurements; Syn: synthetic crRNA & tracrRNA (free of 5'-triphospate); CIP: CIP-treated in-vitro transcript (free of 5'-triphospate); PPP: in-vitro transcript (having 5'-triphospate); N.D.: none detected).

As shown in FIG. 2, the synthetic guide RNA having 5'-OH (that is, free of 5'-triphosphate) or the CIP-treated guide RNA allowed for the expression of IFN-β protein at a level similar to the background level detected in the sample of mock transfection irrespective of treatment with Cas9 protein. In contrast, treatment with the in-vitro transcribed PPP-crRNA/PPP-tracrRNA or PPP-sgRNA increased the level of IFN-β protein to 261 pg/mL. These results indicate the 5'-triphosphate present in the guide RNA of Cas9 RNP induces a Type I interferon response whereas the CIP-treated guide RNA (that is, the 5'-triphosphate-free, in-vitro-transcript) guide RNA) reduces interferon induction.

1.4: Cytopathic Effect

An examination was made of the cytopathic effect caused by a 5'-triphosphated RNA-induced immune response. The synthetic guide RNA, the CIP-treated guide RNA, and the in vitro transcript guide RNA, all prepared in Example 1.1, were delivered, alone and in combination with Cas9 protein, into the HeLa cell line (ATCC). After 72 hrs of incubation, cell viability was quantified using a WST assay (WST based Cell Viability/Cytotoxicity Assay; EZ-Cytox kit (DaeilLab Service Co. Ltd.).

Figure 3:
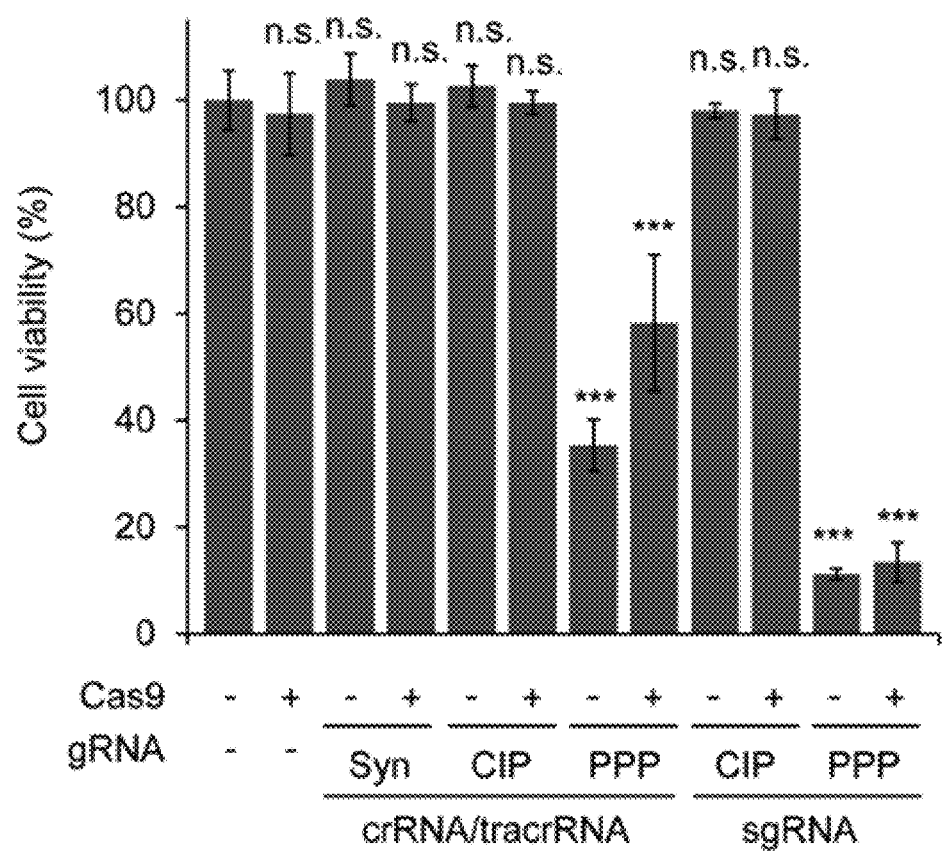
FIG. 3 is a graph showing the results of quantitative analysis of cell viability after the delivery of each of synthetic guide RNA, CIP-treated guide RNA, and in vitro transcribed guide RNA alone or in combination with Cas9 protein into the HeLa cell line (n.s.: not significant; ***: $P<0.001$)

The results are depicted in FIG. 3 (Syn: synthetic crRNA & tracrRNA (free of 5'-triphospate); CIP: CIP-treated in-vitro transcript (free of 5'-triphospate); PPP: in-vitro transcript (having 5'-triphospate) (n.s.: not significant; ***: P<0.001).

A cytopathic effect caused by an immune response was detected only upon treatment with the in-vitro-transcribed PPP-crRNA/PPP-tracrRNA or the PPP-sgRNA. It was also found that the cytopathic effect, which is triggered by in-vitro transcript guide RNA, can be avoided when the CIP-treated guide RNA (that is, when the 5'-triphosphate-free, in-vitro transcript guide RNA) is used.

1.5: Assay for Genome Editing Efficiency

An examination was made of a change in genome editing efficiency when the synthetic guide RNA or the CIP-treated guide RNA was used to avoid an immune response. The guide RNAs prepared in Example 1.1, that is, the synthetic guide RNA, CIP-treated guide RNA, and the in-vitro transcript guide RNA, all targeting an HBB gene, were each subjected, together with Cas9 protein, into RNP delivery into the HeLa cell line (ATCC). After 48 hrs of incubation, genomic DNA was isolated and analyzed for the on-target mutation ratio (insertion/deletion (Indel) %) induced in the HBB gene using next-generation nucleotide sequencing (NGS; Illumina sequencing).

Figure 4:
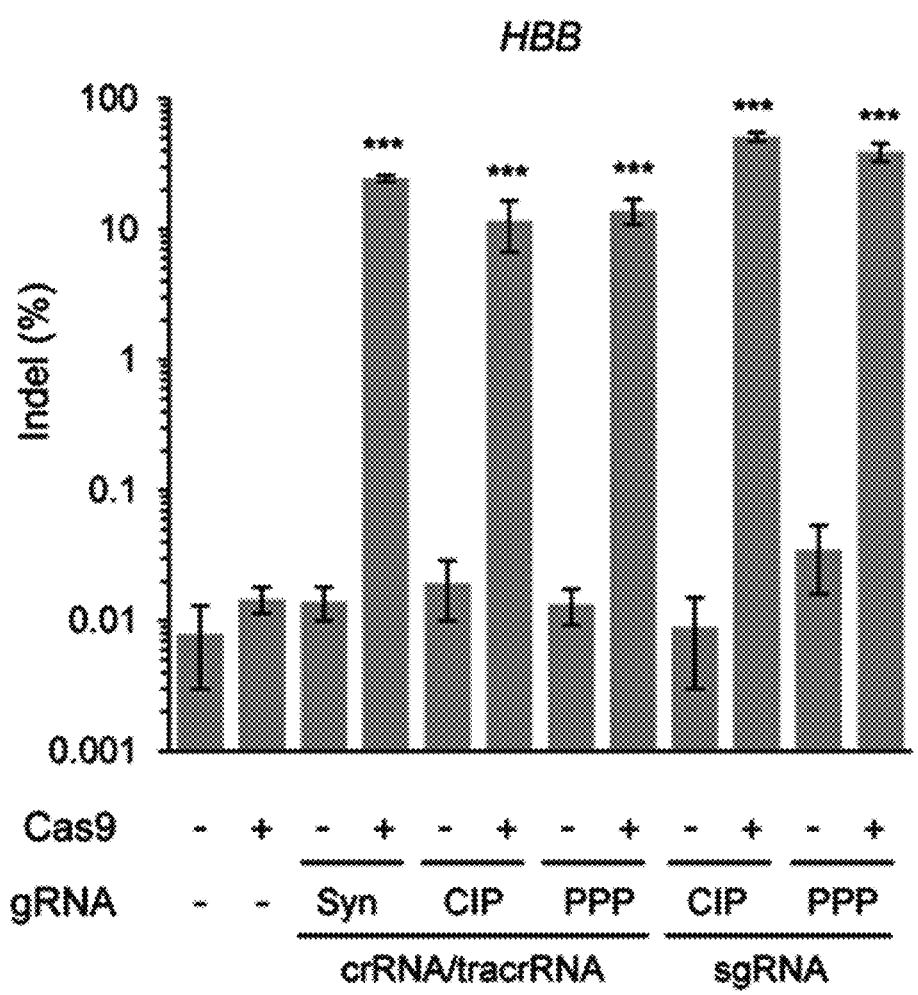
FIG. 4 is a graph showing mutation ratios (Indel (%)) induced in an HBB gene after the RNP delivery of each of synthetic guide RNA, CIP-treated guide RNA, and in vitro transcribed guide RNA, alone or in combination with Cas9 protein, into the HeLa cell line, all of the guide RNAs targeting the HBB gene.

The results are shown in FIG. 4 (Syn: synthetic crRNA & tracrRNA (free of 5'-triphospate); CIP: CIP-treated in vitro transcript (free of 5'-triphospate); PPP: in vitro transcript (having 5'-triphospate)).

As is understood from the data of FIG. 4, the synthetic guide RNA or the CIP-treated guide RNA performed gene editing at an efficiency level similar to that of the conventional in-vitro-transcribed PPP-guide RNA.

Example 2: Cpf1 RNA Delivery 2.1: Preparation of Guide RNA crRNA that targets the DNMT1 gene was prepared through in-vitro transcription (PPP-crRNA) or through a chemical synthesis method (Syn-crRNA).

For the in-vitro transcription, respective oligomers (Table 5) were annealed with corresponding RNAs and then extended using Phusion polymerase (NEB) to give templates, followed by a T7 RNA polymerase (NEB) reaction on the templates.

TABLE 5

Oligomer Sequences as in vitro Transcription Templates

| | | | |
|---|---|---|---|
| crRNA_46nt_F | GAAATTAATACGACTCACTATAGGG | 25 mer | SEQ ID NO: 36 |
| crRNA_46nt_R | GAGTAACAGACATGGACCATCAGATCTACAAGA GTAGAAATTACCCTATAGTGAGTCGTATTAATTTC | 68 mer | SEQ ID NO: 37 |
| crRNA_44nt_F | GAAATTAATACGACTCACTATAG | 23 mer | SEQ ID NO: 38 |
| crRNA_44nt_R | GAGTAACAGACATGGACCATCAGATCTACAAGA GTAGAAATTACTATAGTGAGTCGTATTAATTTC | 66 mer | SEQ ID NO: 39 |

Each of the crRNAs prepared through in-vitro transcription was treated with calf intestinal alkaline phosphatase (CIP) in an amount of 250 U per 200 µl reaction, and subjected to phenol/chloroform extraction. Subsequently, column purification afforded 5'-triphosphate-free RNAs (CIP-crRNA) (Table 6).

TABLE 6

Guide RNA Sequences of RGEN (Cpf1)

| | Sequence (5' - 3') | length | SEQ ID NO: |
|---|---|---|---|
| PPP-crRNA / CIP-crRNA/ Syn-crRNA | GGGUAAUUUCUACUCUUGUAGAU<u>CUG AUGGUCCAUGUCUGUUACUC</u> | 46 nt | 40 |

(underlined: DNMT1-targeting sequence)

2.2: mRNA Level of Genes Involved in Type I Interferon Response

For Cpf1 RNP delivery, an *Acidaminococcus* sp. BV3L6-derived Cpf1 protein (AsCpf1, 5 µg, 25 pmol) was mixed with the DNMT1 gene-targeting crRNA prepared in Example 1.1, that is, (PPP-crRNA, Syn-crRNA, or CIP-crRNA (1.1 µg, 125 pmol). Using a Lipofectamine 2000 (Invitrogen) reagent, transfection into a human HeLa cell line (ATCC) was performed. After 24 hrs of incubation, the cells were lysed to obtain total RNA. After 48 hrs of incubation, genomic DNA was isolated and measured for the efficiency of Cpf1 RNP-derived mutation.

Using the total RNA, RT-qPCR was conducted to measure mRNA levels of IFN-β, RIG-I, and OAS2 genes known to be up-regulated by Type I interferon response. The primers used in the RT-qPCR are summarized in Table 7, below.

TABLE 7

| | | | |
|---|---|---|---|
| Beta-actin-F | CCCAGCCATGTACGTTGCTA (SEQ ID NO: 28) | Beta-actin-R | TCACCGGAGTCCATCACGAT (SEQ ID NO: 29) |
| IFN-b-F | TGCTTCTCCACTACAGCTCTT (SEQ ID NO: 30) | IFN-b-R | GCAGTATTCAAGCCTCCCAT (SEQ ID NO: 31) |
| OAS2-F | TCAGAAGAGAAGCCAACGTGA (SEQ ID NO: 32) | OAS2-R | CGGAGACAGCGAGGGTAAAT (SEQ ID NO: 33) |
| RIG-1-F | GGACGTGGCAAAACAAATCAG (SEQ ID NO: 34) | RIG-1-R | GCAATGTCAATGCCTTCATCA (SEQ ID NO: 35) |

Figure 5A:
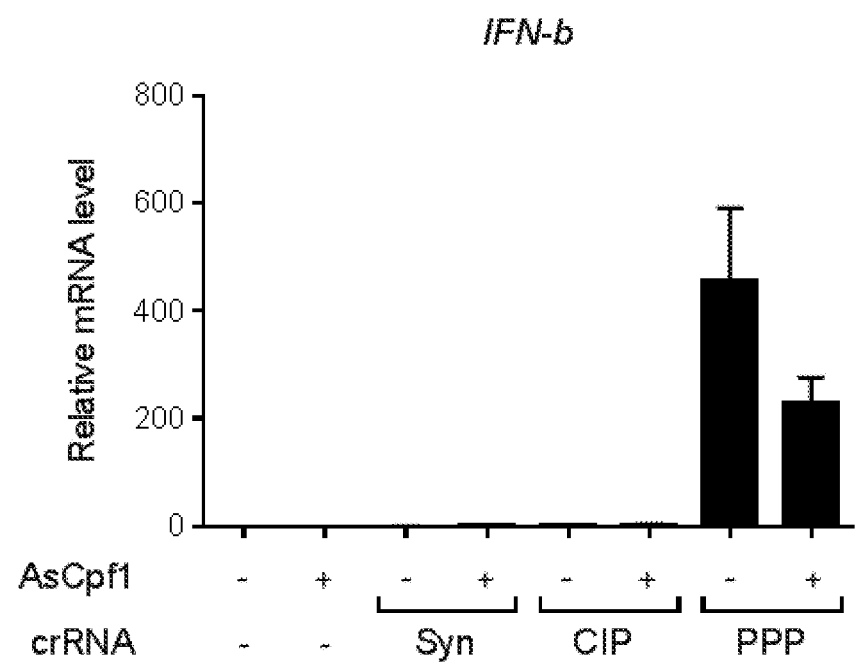
FIG. 5A is a graph showing IFN-6 mRNA levels after the delivery of synthetic guide RNA, CIP-treated guide RNA, and in vitro transcribed guide RNA alone or in combination with Cpf1 protein into the HeLa cell line, as measured by RT-qPCR.

Expression levels of the genes (mRNA levels) are depicted in FIGS. 5A (IFN-β), 5B (RIG-I), and 5C (OAS2) (Syn: synthetic crRNA (free of 5'-triphospate); CIP: CIP-treated in vitro transcript (free of 5'-triphospate); PPP: in vitro transcript (having 5'-triphospate)).

Figure 5B:
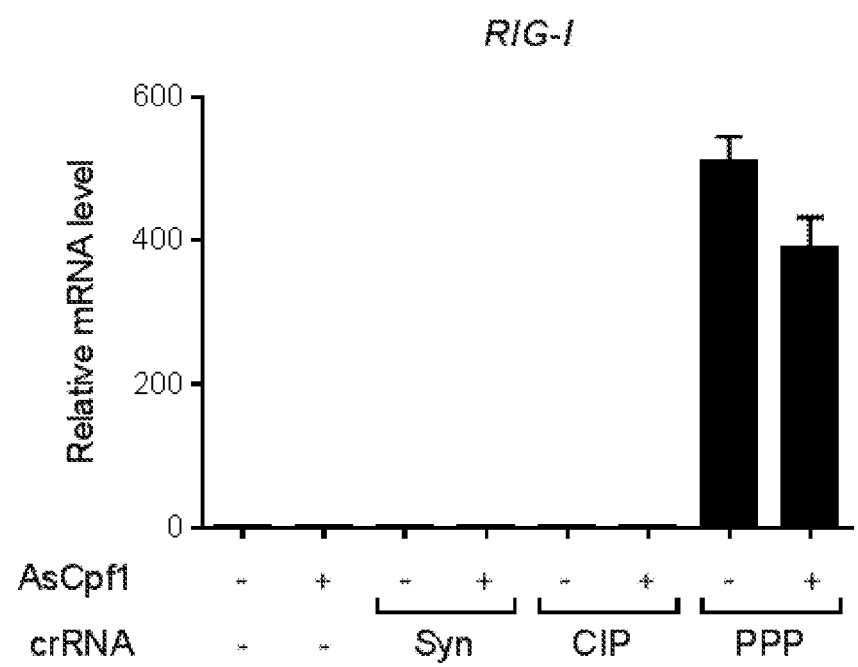
FIG. 5B is a graph showing RIG-I mRNA levels after the delivery of synthetic guide RNA, CIP-treated guide RNA, and in vitro transcribed guide RNA alone or in combination with Cpf1 protein into the HeLa cell line, as measured by RT-qPCR.
Figure 5C:
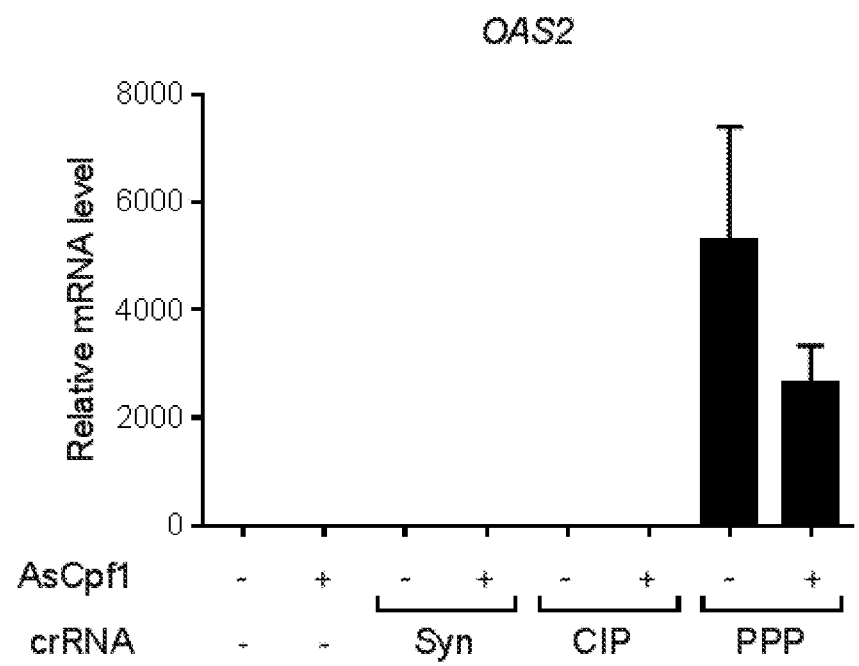
FIG. 5C is a graph showing OAS2 mRNA levels after the delivery of synthetic guide RNA, CIP-treated guide RNA, and in vitro transcribed guide RNA into the HeLa cell line, as measured by RT-qPCR.

As shown in FIGS. 5A-5C, the synthetic guide RNA or the CIP-treated guide RNA, both having 5'-OH (that is, free of 5'-triphosphate), allowed IFN-β, RIG-I, and OAS2 genes to be expressed in levels similar to the background level detected in the sample of mock transfection, regardless of whether the Cpf1 protein was used. In contrast, treatment with the in-vitro-transcribed PPP-crRNA/PPP-tracrRNA or PPP-sgRNA remarkably increased the expression (mRNA) of each of IFN-β, RIG-I, and OAS2 genes. These results indicate the 5'-triphosphate present in the guide RNA of Cpf1 RNP induces Type I interferon response. It was also observed that the synthetic RNA or the CIP-treated guide RNA can be used to avoid the immune response.

2.3: Assay for Genome Editing Efficiency

An examination was made of a change in genome editing efficiency when the synthetic guide RNA or the CIP-treated guide RNA was used to avoid an immune response. The guide RNAs prepared in Example 2.1, that is, the synthetic guide RNA, CIP-treated guide RNA, and the in-vitro transcript guide RNA, all targeting a DNMT1 gene, were each subjected, together with Cpf1 protein, into RNP delivery into the HeLa cell line (ATCC). After 48 hrs of incubation, genomic DNA was isolated and analyzed for the on-target mutation ratio (insertion/deletion (Indel) %) induced in the DNMT1 gene using next-generation nucleotide sequencing (NGS; Illumina sequencing).

Figure 6:
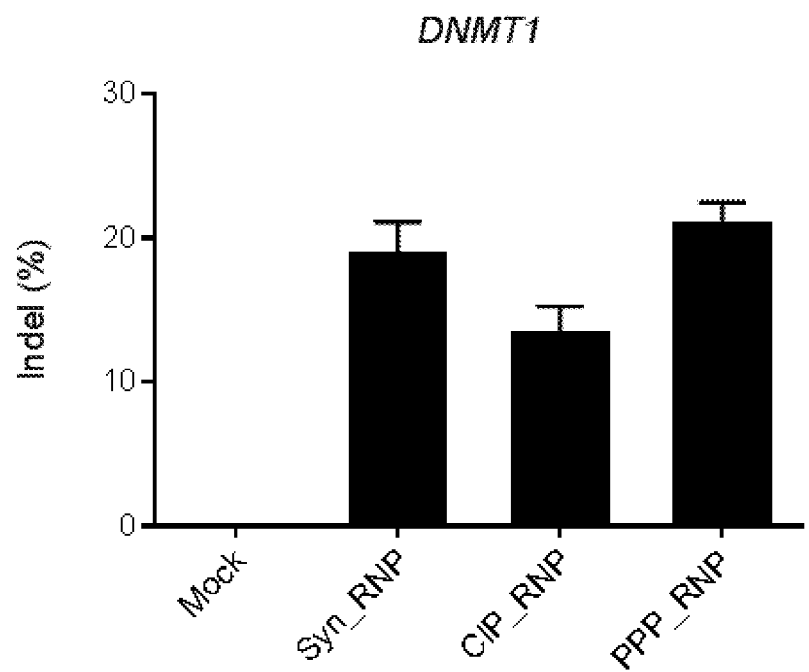
FIG. 6 is a graph showing mutation ratios (Indel (%)) induced in a DNMT1 gene after the RNP delivery of each of synthetic guide RNA, CIP-treated guide RNA, and in vitro transcribed guide RNA, alone or in combination with Cas9 protein, into the HeLa cell line, all of the guide RNAs targeting the DNMT1 gene.

The results are shown in FIG. 6 (Syn: synthetic crRNA & tracrRNA (free of 5'-triphospate); CIP: CIP-treated in vitro transcript (free of 5'-triphospate); PPP: in vitro transcript (having 5'-triphospate)).

As is understood from the data of FIG. 6, the synthetic guide RNA or the CIP-treated guide RNA performed gene editing at an efficiency level similar to that of the conventional in-vitro-transcribed PPP-guide RNA.

The invention claimed is:

1. A method of decreasing expression of a gene involved in a Type I interferon response following delivery of an RNA-guided endonuclease ribonucleoprotein into a cell wherein the cell comprises the gene involved in the Type I interferon response, the method comprising preparing a guide RNA having a 5' end free of both a diphosphate residue and a triphosphate residue by in vitro transcription using a prokaryote RNA polymerase followed by removing the diphosphate and the triphosphate residues of the guide RNA, forming the RNA-guided endonuclease ribonucleoprotein by combining a Cpf1 protein with the guide RNA having the 5' end free of both the diphosphate residue and the triphosphate residue, administering the RNA-guided endonuclease ribonucleoprotein directly to the cell, and wherein the gene involved in the Type I interferon response comprises a gene selected from the group consisting of IFN-β (Interferon-beta), RIG-1 (retinoic acid-inducible gene 1), and OAS2 (2'-5'-oligoadenylate synthetase 2) genes, and the expression level of the gene involved in the type I interferon response is decreased compared to a control in which a RNA-guided endonuclease ribonucleoprotein comprising a Cpf1 protein and a guide RNA having the diphosphate residue or the triphosphate residue at the 5' end is administered.

2. The method of claim 1, wherein the Cpf1 protein is obtained from Parcubacteria bacterium, Peregrinibacteria bacterium, *Acidaminococcus* sp., *Porphyromonas macacae*, Lachnospiraceae bacterium, *Porphyromonas crevioricanis*, *Prevotella disiens, Moraxella bovoculi, Leptospira inadai,* Lachnospiraceae bacterium (MA2020), *Francisella novicida, Candidatus methanoplasma termitum,* or *Eubacterium eligens*.

3. The method of claim 1, wherein the prokaryotic RNA polymerase is a bacteriophage RNA polymerase.

4. The method of claim 3, wherein the bacteriophage RNA polymerase is at least one selected from the group consisting of T7 RNA polymerase, T3 RNA polymerase, and SP6 RNA polymerase.

5. A method of decreasing expression of a gene involved in a Type I interferon response following delivery of an RNA-guided endonuclease ribonucleoprotein into a cell wherein the cell comprises the gene involved in the Type I interferon response, the method comprising preparing a guide RNA by in vitro transcription using a prokaryote RNA polymerase followed by removing the diphosphate and the triphosphate residues of the guide RNA, forming the RNA-guided endonuclease ribonucleoprotein by combining a Cas9 protein with the guide RNA having the 5' end free of both the diphosphate residue and the triphosphate residue, administering the RNA-guided endonuclease ribonucleoprotein directly to the cell, wherein the guide RNA comprises CRISPR RNA (crRNA) and trans-activating crRNA (tracrRNA), and wherein the gene involved in the Type I interferon response is comprises a gene selected from the group consisting of IFN-β, RIG 1, and OAS2 genes, and the expression level of the gene involved in the type I interferon response is decreased compared to a control in which a RNA-guided endonuclease ribonucleoprotein comprising a Cas9 protein and a guide RNA having the diphosphate residue or the triphosphate residue at the 5' end is administered.

6. The method of claim 5, wherein the prokaryotic RNA polymerase is a bacteriophage RNA polymerase.

* * * * *

SEQUENCE LISTING

<160> NUMBER OF SEQ ID NOS: 40

<210> SEQ ID NO 1
<211> LENGTH: 12
<212> TYPE: RNA
<213> ORGANISM: Artificial Sequence
<220> FEATURE:
<223> OTHER INFORMATION: nucleic acid sequence of an essential part of
      crRNA for Cas9

<400> SEQUENCE: 1
guuuuagagc ua                                                         12

<210> SEQ ID NO 2
<211> LENGTH: 10
<212> TYPE: RNA
<213> ORGANISM: Artificial Sequence
<220> FEATURE:
<223> OTHER INFORMATION: 3'-terminal sequence of  crRNA for Cas9

<400> SEQUENCE: 2
ugcuguuuug                                                            10

<210> SEQ ID NO 3
<211> LENGTH: 60
<212> TYPE: RNA
<213> ORGANISM: Artificial Sequence
<220> FEATURE:
<223> OTHER INFORMATION: nucleic acid sequence of an essential part of
      tracrRNA for Cas9

<400> SEQUENCE: 3
uagcaaguua aaauaaggcu aguccguuau caacuugaaa aaguggcacc gagucggugc      60

<210> SEQ ID NO 4
<211> LENGTH: 21
<212> TYPE: RNA
<213> ORGANISM: Artificial Sequence
<220> FEATURE:
<223> OTHER INFORMATION: 5'-terminal sequence of crRNA for Cpf1
<220> FEATURE:
<221> NAME/KEY: misc_feature
<222> LOCATION: (1)
<223> OTHER INFORMATION: n is U, A, G, or absent
<220> FEATURE:
<221> NAME/KEY: misc_feature

```
<222> LOCATION: (2)
<223> OTHER INFORMATION: n is A or Gn
<220> FEATURE:
<221> NAME/KEY: misc_feature
<222> LOCATION: (5)
<223> OTHER INFORMATION: n is U, A, or C
<220> FEATURE:
<221> NAME/KEY: misc_feature
<222> LOCATION: (12)
<223> OTHER INFORMATION: n is absent, G, C, or A
<220> FEATURE:
<221> NAME/KEY: misc_feature
<222> LOCATION: (13)
<223> OTHER INFORMATION: n is A, U, C, or G

<400> SEQUENCE: 4
nnaunucuac unnuuguaga u                                          21

<210> SEQ ID NO 5
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (PbCpi1)

<400> SEQUENCE: 5
aaauuucuac uuuuguagau                                            20

<210> SEQ ID NO 6
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (PeCpf1)

<400> SEQUENCE: 6
ggauuucuac uuuuguagau                                            20

<210> SEQ ID NO 7
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (AsCpf1)

<400> SEQUENCE: 7
uaauuucuac ucuuguagau                                            20

<210> SEQ ID NO 8
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (PmCpf1)

<400> SEQUENCE: 8
uaauuucuac uauuguagau                                            20

<210> SEQ ID NO 9
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (LbCpi1)

<400> SEQUENCE: 9
gaauuucuac uauuguagau                                            20
```

```
<210> SEQ ID NO 10
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (PcCpf1)

<400> SEQUENCE: 10
uaauuucuac uauuguagau                                                 20

<210> SEQ ID NO 11
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (PdCpf1)

<400> SEQUENCE: 11
uaauuucuac uucgguagau                                                 20

<210> SEQ ID NO 12
<211> LENGTH: 21
<212> TYPE: RNA
<213> ORGANISM: Artificial Sequence
<220> FEATURE:
<223> OTHER INFORMATION: 5'-terminal sequence of crRNA for Cpf1 (MbCpf1)

<400> SEQUENCE: 12
aaauuucuac uguuguaga u                                                21

<210> SEQ ID NO 13
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (LiCpf1)

<400> SEQUENCE: 13
gaauuucuac uuuuguagau                                                 20

<210> SEQ ID NO 14
<211> LENGTH: 20
<212> TYPE: RNA
<213> ORGANISM: Artificial Sequence
<220> FEATURE:
<223> OTHER INFORMATION: 5'-terminal sequence of crRNA for Cpf1
      (Lb2Cpf1)

<400> SEQUENCE: 14
gaauuucuac uauuguagau                                                 20

<210> SEQ ID NO 15
<211> LENGTH: 20
<212> TYPE: RNA
<213> ORGANISM: Artificial Sequence
<220> FEATURE:
<223> OTHER INFORMATION: 5'-terminal sequence of crRNA for Cpf1 (FnCpf1)

<400> SEQUENCE: 15
uaauuucuac uguuguagau                                                 20

<210> SEQ ID NO 16
<211> LENGTH: 21
<212> TYPE: RNA
<213> ORGANISM: Artificial Sequence
<220> FEATURE:
```

<223> OTHER INFORMATION: 5'-terminal sequence of crRNA for Cpf1
    (CMtCpf1)

<400> SEQUENCE: 16
gaaucucuac ucuuuguaga u                                         21

<210> SEQ ID NO 17
<211> LENGTH: 19
<212> TYPE: RNA
<213> ORGANISM: Artificial Sequence
<220> FEATURE:
<223> OTHER INFORMATION: 5'-terminal sequence of crRNA for Cpf1 (EeCpf1)

<400> SEQUENCE: 17
uaauuucuac uuuguagau                                            19

<210> SEQ ID NO 18
<211> LENGTH: 65
<212> TYPE: DNA
<213> ORGANISM: Artificial Sequence
<220> FEATURE:
<223> OTHER INFORMATION: transcriptional template for sgRNA_F for Cas9

<400> SEQUENCE: 18
gaaattaata cgactcacta gtttgcccc acagggcagt aagttttaga gctagaaata    60
gcaag                                                              65

<210> SEQ ID NO 19
<211> LENGTH: 82
<212> TYPE: DNA
<213> ORGANISM: Artificial Sequence
<220> FEATURE:
<223> OTHER INFORMATION: transcriptional template for sgRNA_R for Cas9

<400> SEQUENCE: 19
aaaaaagcac cgactcggtg ccacttttc aagttgataa cggactagcc ttatttaac    60 ttgctatttc tagctctaaa ac                                           82

<210> SEQ ID NO 20
<211> LENGTH: 64
<212> TYPE: DNA
<213> ORGANISM: Artificial Sequence
<220> FEATURE:
<223> OTHER INFORMATION: transcriptional template for crRNA_F for Cas9

<400> SEQUENCE: 20
gaaattaata cgactcacta gtttgcccc acagggcagt aagttttaga gctatgctgt    60
tttg                                                               64

<210> SEQ ID NO 21
<211> LENGTH: 64
<212> TYPE: DNA
<213> ORGANISM: Artificial Sequence
<220> FEATURE:
<223> OTHER INFORMATION: transcriptional template for crRNA_R for Cas9

<400> SEQUENCE: 21
caaaacagca tagctctaaa acttactgcc ctgtggggca actatagtga gtcgtattaa    60
tttc                                                               64

<210> SEQ ID NO 22
<211> LENGTH: 67
<212> TYPE: DNA

```
<213> ORGANISM: Artificial Sequence
<220> FEATURE:
<223> OTHER INFORMATION: transcriptional template for tracRNA_F for Cas9

<400> SEQUENCE: 22
gaaattaata cgactcacta taggaaccat tcaaaacagc atagcaagtt aaaataaggc        60
tagtccg                                                                  67

<210> SEQ ID NO 23
<211> LENGTH: 69
<212> TYPE: DNA
<213> ORGANISM: Artificial Sequence
<220> FEATURE:
<223> OTHER INFORMATION: transcriptional template for tracRNA_R for Cas9

<400> SEQUENCE: 23
aaaaaaagca ccgactcggt gccactttt caagttgata acggactagc cttattttaa         60
cttgctatg                                                                69

<210> SEQ ID NO 24
<211> LENGTH: 102
<212> TYPE: RNA
<213> ORGANISM: Artificial Sequence
<220> FEATURE:
<223> OTHER INFORMATION: an example of sgRNA for Cas9

<400> SEQUENCE: 24
guugccccac agggcaguaa guuuuagagc uagaaauagc aaguuaaaau aaggcuaguc        60
cguuaucaac uugaaaaagu ggcaccgagu cggugcuuuu uu                          102

<210> SEQ ID NO 25
<211> LENGTH: 42
<212> TYPE: RNA
<213> ORGANISM: Artificial Sequence
<220> FEATURE:
<223> OTHER INFORMATION: an example of crRNA for Cas9

<400> SEQUENCE: 25
guugccccac agggcaguaa guuuuagagc uaugcuguuu ug                           42

<210> SEQ ID NO 26
<211> LENGTH: 86
<212> TYPE: RNA
<213> ORGANISM: Artificial Sequence
<220> FEATURE:
<223> OTHER INFORMATION: an example of tracrRNA for Cas9

<400> SEQUENCE: 26
ggaaccauuc aaaacagcau agcaaguuaa aauaaggcua guccguuauc aacuugaaaa        60
aguggcaccg agucggugcu uuuuu                                              86

<210> SEQ ID NO 27
<211> LENGTH: 69
<212> TYPE: RNA
<213> ORGANISM: Artificial Sequence
<220> FEATURE:
<223> OTHER INFORMATION: an example of synthetic tracrRNA for Cas9

<400> SEQUENCE: 27
aaacagcaua gcaaguuaaa auaaggcuag uccguuauca acuugaaaaa guggcaccga        60
gucggugcu                                                                69
```

```
<210> SEQ ID NO 28
<211> LENGTH: 20
<212> TYPE: DNA
<213> ORGANISM: Artificial Sequence
<220> FEATURE:
<223> OTHER INFORMATION: Beta-actin-F primer

<400> SEQUENCE: 28
cccagccatg tacgttgcta                                               20

<210> SEQ ID NO 29
<211> LENGTH: 20
<212> TYPE: DNA
<213> ORGANISM: Artificial Sequence
<220> FEATURE:
<223> OTHER INFORMATION: Beta-actin-R primer

<400> SEQUENCE: 29
tcaccggagt ccatcacgat                                               20

<210> SEQ ID NO 30
<211> LENGTH: 21
<212> TYPE: DNA
<213> ORGANISM: Artificial Sequence
<220> FEATURE:
<223> OTHER INFORMATION: IFN-b-F primer

<400> SEQUENCE: 30
tgcttctcca ctacagctct t                                             21

<210> SEQ ID NO 31
<211> LENGTH: 20
<212> TYPE: DNA
<213> ORGANISM: Artificial Sequence
<220> FEATURE:
<223> OTHER INFORMATION: IFN-b-R primer

<400> SEQUENCE: 31
gcagtattca agcctcccat                                               20

<210> SEQ ID NO 32
<211> LENGTH: 21
<212> TYPE: DNA
<213> ORGANISM: Artificial Sequence
<220> FEATURE:
<223> OTHER INFORMATION: OAS2- F primer

<400> SEQUENCE: 32
tcagaagaga agccaacgtg a                                             21

<210> SEQ ID NO 33
<211> LENGTH: 20
<212> TYPE: DNA
<213> ORGANISM: Artificial Sequence
<220> FEATURE:
<223> OTHER INFORMATION: OAS2- R primer

<400> SEQUENCE: 33
cggagacagc gagggtaaat                                               20

<210> SEQ ID NO 34
<211> LENGTH: 21
<212> TYPE: DNA
<213> ORGANISM: Artificial Sequence
<220> FEATURE:
<223> OTHER INFORMATION: RIG-1-F primer
```

<400> SEQUENCE: 34
ggacgtggca aaacaaatca g                                               21

<210> SEQ ID NO 35
<211> LENGTH: 21
<212> TYPE: DNA
<213> ORGANISM: Artificial Sequence
<220> FEATURE:
<223> OTHER INFORMATION: RIG-1-R primer

<400> SEQUENCE: 35
gcaatgtcaa tgccttcatc a                                               21

<210> SEQ ID NO 36
<211> LENGTH: 25
<212> TYPE: DNA
<213> ORGANISM: Artificial Sequence
<220> FEATURE:
<223> OTHER INFORMATION: transcriptional template of crRNA_46nt_F for
      Cpf1

<400> SEQUENCE: 36
gaaattaata cgactcacta taggg                                           25

<210> SEQ ID NO 37
<211> LENGTH: 68
<212> TYPE: DNA
<213> ORGANISM: Artificial Sequence
<220> FEATURE:
<223> OTHER INFORMATION: transcriptional template of crRNA_46nt_R for
      Cpf1

<400> SEQUENCE: 37
gagtaacaga catggaccat cagatctaca agagtagaaa ttaccctata gtgagtcgta     60
ttaatttc                                                              68

<210> SEQ ID NO 38
<211> LENGTH: 23
<212> TYPE: DNA
<213> ORGANISM: Artificial Sequence
<220> FEATURE:
<223> OTHER INFORMATION: transcriptional template of crRNA_44nt_F for
      Cpf1

<400> SEQUENCE: 38
gaaattaata cgactcacta tag                                             23

<210> SEQ ID NO 39
<211> LENGTH: 66
<212> TYPE: DNA
<213> ORGANISM: Artificial Sequence
<220> FEATURE:
<223> OTHER INFORMATION: transcriptional template of crRNA_44nt_R for
      Cpf1

<400> SEQUENCE: 39
gagtaacaga catggaccat cagatctaca agagtagaaa ttactatagt gagtcgtatt     60
aatttc                                                                66

<210> SEQ ID NO 40
<211> LENGTH: 46
<212> TYPE: RNA
<213> ORGANISM: Artificial Sequence
<220> FEATURE:
<223> OTHER INFORMATION: an example of crRNA (46nt) for Cpf1

```
<400> SEQUENCE: 40
ggguaauuuc uacucuugua gaucugaugg uccaugucug uuacuc        46
```